United States Patent [19]
Olstein

[11] Patent Number: 5,142,010
[45] Date of Patent: Aug. 25, 1992

[54] POLYMERIC BIOCIDAL AGENTS

[75] Inventor: Alan D. Olstein, Mendota Heights, Minn.

[73] Assignee: H. B. Fuller Licensing & Financing Inc., Wilmington, Del.

[21] Appl. No.: 521,376

[22] Filed: May 10, 1990

[51] Int. Cl.$^5$ .............................................. C08F 26/00
[52] U.S. Cl. ................................... 526/248; 526/310; 526/312; 560/163; 560/221; 562/439; 564/164
[58] Field of Search ............... 560/163, 221; 562/439; 564/164; 526/248, 310, 312

[56] References Cited

U.S. PATENT DOCUMENTS

| | | | |
|---|---|---|---|
| 3,444,242 | 5/1969 | Rue et al. | 260/611 |
| 3,483,141 | 12/1969 | Litt et al. | 260/2 |
| 3,483,145 | 12/1969 | Levy et al. | 260/2 |
| 3,560,507 | 2/1971 | Wakeman et al. | 260/286 |
| 3,579,630 | 5/1971 | Herz et al. | 424/47 |
| 3,821,399 | 6/1974 | Richter | 424/304 |
| 3,879,541 | 4/1975 | Krabbe et al. | 514/635 |
| 3,996,232 | 12/1976 | Diamond et al. | 562/439 |

OTHER PUBLICATIONS

Kirk-Othmer, *Encyclopedia of Chemical Technology*, 1984, "Guanidine and Guanidine Salts", pp. 514-521.
Coburn, *Journal of Medicinal Chemistry*, 1978, vol. 21, No. 8, "In Vitro Antiplaque Properties of a Series of Alkyl Bis(biguanides)", pp. 828-829.
Ikeda, Yamaguchi and Tazuke, *Journal of Bioactive and Compatible Polymers*, "Self-Sterilizing Materials. 1. Controlled Release of Biguanide Biocides from Polymeric Materials", vol. 1, Apr. 1986, pp. 162-171.
Ikeda, Yamaguchi and Tazuke, *Journal of Bioactive and Compatible Polymers*, "Self-Sterilizing Marterials. 2. Evaluation of Surface Antibacterial Activity", vol. 1, Jul. 1986, pp. 301-308.
Ikeda, Yamaguchi and Tazuke, *Antimicrobial Agents and Chemother.*, "New Polymeric Biocides: Synthesis and Antibacterial Activities of Polycations with Pendant Biguanide Groups", vol. 26, No. 2, pp. 139-143.
Endo, Tani and Kodama, *Applied and Environmental Microbiology*, Sep. 1987, "Antimicrobial Activity of Tertiary Amine Covalently Bonded to a Polystyrene Fiber", vol. 53, No. 9, pp. 2050-2055.
Hudson, Ojo and Planka, *International Pest Control*, 28 (6) 1986, "Guanidines With Antifungal (and Antibacterial) Activity—a Review", pp. 148-149, 152-155.
Warner, Lynch and Ajemian, *Journal of Pharmaceutical Sciences*, "Synthesis, Physicochemical Parameters, and In Vitro Evaluation of $N^1$-p-Chlorophenyl-$N^5$ Alkylbiguanides", pp. 1070-1072.
Data sheet on Fluorad ® (from 3M).
Paul et al., *Indian J. Chem.*, 1, pp. 218-310 (1963); Basu et al., *Indian J. Pharm.*, 23, pp. 124-125 (1961) (Abstracts Only).
Bliznyukov et al., *Zh. Obshch. Kkim.*, 34 (1), pp. 329-331, (1964), (Abstract Only).
Abstract No. 137775j, *Chemical Abstracts*, (Abstract Only), Yuki et al., vol. 90, No. 17, p. 511.
Abstract No. 184445z, *Chemical Abstracts*, (Abstract Only), Yuki et al., vol. 87, No. 23, p. 607.

*Primary Examiner*—Paul R. Michl
*Assistant Examiner*—LaVonda R. DeWitt
*Attorney, Agent, or Firm*—Merchant, Gould, Smith, Edell. Welter & Schmidt

[57] ABSTRACT

An antimicrobial polymerizable compound and polymers resulting therefrom, the compound being

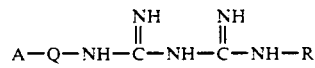

wherein A is any polymerizable group; Q is phenylene; and R is $-(CF_2)_yCF_3$ wherein $y=1$-20, $-(CH_2)_x-O-C_xH_{2x+1}$ wherein $x=1$-25, $-(CH_2CH_2O)_n(CH_2CHCH_3O)_m(CH_2CH_2O)_pT$ wherein $T=-H$ or any branched or unbranched $C_{1-20}$ alkyl and n, m, and $p=0$-99 and $m+n+p \geqq 1$, $-CHR'COOH$ wherein $R'$ is H or any naturally occurring amino acid side chain, $-(CH_2)_xCOOH$, $-(CH_2)_x-(CH_2CH_2-O)_n-(CH_2CHCH_3O)_m(CH_2CH_2O)_p-CO-NH-CH_2-CH=CH_2$, $-(CH_2)_x-CO-NH-CH_2-CH=CH_2$, or $-(CH_2)_x-O-C-COH=CH_2$. The resulting polymers are useful in any variety of applications requiring an antimicrobial agent or an active sanitizer or disinfectant including caulks, mortars, films and coatings, adhesives and the like. The polymers of this invention are also useful in medical, food preparation and personal care product applications.

58 Claims, No Drawings

POLYMERIC BIOCIDAL AGENTS

FIELD OF THE INVENTION

The invention relates to a novel polymeric biocidal, antibacterial or antimicrobial agent, and to monomers used in the preparation of the polymeric agents. The polymer materials of the invention can be used in biocidal, antibacterial or antimicrobial applications, such as surface sanitizing, the stabilization of compositions to microbial action, food preservation, medical-surgical application, general antimicrobial or antiseptic uses, and others. The novel antibacterial agents of the invention can be used in the form of bulk polymer, in fiber, films, or fabrics as a solution or emulsion in common aqueous or organic solvents.

BACKGROUND OF THE INVENTION

The inappropriate growth of a variety of organisms has been a problem for many years. Unicellular and multi-cellular organisms have caused degradation of natural product materials, infection in humans and other animals, spoilage of foods, chemical degradation of synthetic materials. Micro and macroorganisms have also been known to foul surfaces in aqueous marine and production environments. Such growth can result in the failure of the attached substrate to properly perform in their intended use locus and further may lead to infection and disease within mammals.

Antimicrobial agents have been combined with film-forming polymeric materials and have been used in the absence of a polymeric carrier, for example, chlorguanide, [1-(p-chlorophenyl)-5-isopropyl biguanide has been used as an antimalarial agent. Similarly, chlorhexadene, [1,1'-hexamethylenebis-5-para-p-chlorophenyl biguanide] is well known as a topical antiseptic.

U.S. Pat. No. 3,325,436 discloses bacterial resistant latexes that incorporate alpha,alpha'-azobis(chloroformamadine). U.S. Pat. No. 2,689,837 discloses polymeric vinyl halides having improved resistance to deterioration caused by fungal and bacterial attack, which incorporate copper 8-quinolinolate into the polymer.

U.S. Pat. No. 3,577,516 discloses a spray-on bandage material using acrylate or methacrylate polymers that may contain germicides or fungicides. Phenols and thiophenols are well-known antimicrobial agents and have been incorporated into polymeric compounds.

U.S. Pat. No. 2,875,097 discloses the incorporation of phenolic compounds into polymers comprising heterocyclic nitrogen compounds. These polymers are typically used to render fabrics resistant to fungi and insect attack. U.S. Pat. No. 2,873,263 discloses an antibacterial polymeric resin used for fabricating plastic articles. These resins are formed by polymerizing an unsaturated monomer such as an alkyl acrylate in the presence of certain aromatic phenols or phenolic analogs.

Compositions intended for the controlled release of a disinfectant from a film of stabilized hydrophilic polymer are disclosed in U.S. Pat. No. 3,966,902. The polymer complexes are stabilized as a metal complex by the addition of an inorganic aluminum, zirconium or zinc salt, such as aluminum chlorhydro, to the polymerization mixture. The stabilization adjuvant is necessary because, upon contact with water, such films of simple hydrogels become highly swollen and rapidly elute their additives. Further, dry films, both simple and metal complexed hydrogels, do not adhere well to ceramic and other hard surfaces and can lose their adhesion completely when wetted.

The incorporation of various biocides into polymeric base material either by mixing, physical entrainment, ionic complexation, or copolymerization has as yet not satisfactorily addressed the problem of providing polymeric compositions capable of potent prolonged antimicrobial action without significant release of toxic materials.

Therefore, a continuing need exists for an antimicrobial composition capable of producing an ongoing biodegradable biocidal agent in sufficient concentration to provide a surface substantially free of organisms.

BRIEF DESCRIPTION OF THE INVENTION

The invention provides a polymer composition that can prevent microbial growth through the presence of strong biocidal groups in the polymer. The present invention provides an antimicrobial composition comprising a polymer, including copolymers, terpolymers, oligomers and the like, having a pendent-active functional group according to the following general formula (I):

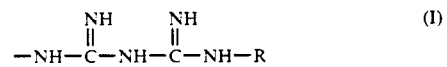

wherein R is a common amine substituent such as $-(CF_2)_yCF_3$ wherein $y = 1-20$, $-(CH_2)_xO-C_xH_{2x+1}$ wherein $x = 1-25$, $-(CH_2CH_2O)_n(CH_2CHCH_3O)_m(CH_2CH_2O)_pT$ wherein $T = $ H or an unbranched or branched $C_{1-20}$ alkyl such as methyl, or t-butyl, n, m and $p = 0-99$ and $m+n+p \geq 1$ $-CHR'COOH$ wherein R' is any naturally occurring amino acid side chain, $-(CH_2)_xCOOH$,

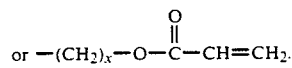

The monomer must contain the unsymmetrical biguanide group (I), and a polymerizable group attached to the active biguanide group according to the following formula (II):

wherein Q generally is phenylene, R is as defined above and A is a polymerizable group including any polymerizable active hydrogen containing group such as alkoxy silane moieties; isocyanate moieties; polymerizable vinyl moieties such as n-allyl amine; an epoxy group like

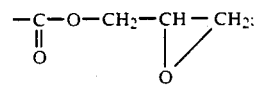

an aziridine group like

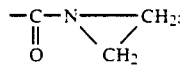

a polymerizable moiety containing an active hydrogen like —H, —OH, —NH$_2$, —COOH, or (CH$_2$)$_x$R" wherein R" is —H, —OH, —NH$_2$, —COOH; or an amide like

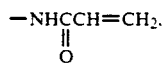

The polymeric material of this invention has inherent biocidal activity and can be used as an additive to substances subject to microbial attack such as a surface coating on fiber, fabric, film and other hard surfaces for the purpose of providing antimicrobial resistance to the surface. The polymeric material of the invention can also be used as a structured material in bulk polymeric fiber, fabric, film or other objects made from polymeric materials.

One particularly useful advantage of the polymeric materials of the invention is that the monomers can be incorporated into polymers which are useful as the structured polymer in a film, coating, or sealant such as an adhesive. The resulting product is inherently resistant to the degradation caused by the growth of organisms. Such films or sealants can take the form of hot melts, thermosets, aqueous-based thermosetting adhesives, aqueous-based thermoplastic adhesives, solvents, cements, two or multipart adhesive compositions, etc. The present invention may also be used in paints, caulks, cementatious materials, coating and the like. These compositions, per se, during manufacture, storage and use are resistant to the inappropriate attack by microbes on the polymer material.

Further, after application and the formation of an adhesive bond, the inherent antimicrobial nature of the material prevents degradation of the bond line due to attack by microbial populations. Such antimicrobial characteristics can extend to adjacent substrate materials in contact with the adhesive. Further advantages can be obtained by preparing the substrate from materials derived from the polymer or modified by the polymer to form antimicrobial substrate.

The polymer containing the pendent group (I) can take the form of a vinyl polymer, a polyester, a polyalkoxy compound, a polyamine compound, a graft copolymer, etc. The monomer can be used in the manufacture of the polymer used in a functional material, such as a bulk polymer, a dispersion, fiber, fabric, film, etc. The polymeric material can be dissolved in a suitable solvent and the resulting solution can be added to the use locus or coated on a fiber, fabric, film or other surface. The composition may be applied to a target surface by spraying, wiping, pouring, dipping and the like. The resultant films that can form after solvent removal are clear, adherent, and are resistant to abrasion in the sense that they are not readily removed when the surface is wiped, sprayed or contacted mechanically.

Polymeric materials, whether in solution, dispersion or as a bulk polymer having the pendent group (I) can be a homopolymer, a copolymer (a polymeric material having two or more monomer constituents), an oligomer (a relatively low molecular weight polymer), or a terpolymer (a polymeric material having three or more monomers).

The invention also relates to a method of stabilizing a polymer dispersion, a film fiber, a bulk polymer or disinfecting a surface with a polymer containing pendent groups according to Formula (I).

DETAILED DESCRIPTION OF THE INVENTION

The novel polymeric materials of the invention can be prepared by known polymerization techniques from vinyl monomers, epoxy monomers, aziridine monomers, and the like. Generally these polymeric materials can be directly blended with compositions for the purpose of imparting antimicrobial properties of the compositions. Vinyl, epoxy, polyamine, and the like polymers can be made incorporating the biguanide substituent into the polymer material which can form the active or structural material in adhesive compositions, fibers, fabrics, films, bulk polymers, coating systems, and sealants among other products.

The polymeric materials of the invention can be used as an additive to compositions that are subject to biological degradation caused by the growth of organisms. As such, the material is used at relatively low proportions, typically less than 10 wt-%, preferably less than 5 wt-% based on the bulk material. The polymer material of the invention can be used to treat bulk polymers, treat aqueous polymeric dispersions, coat fabrics, fibers, or films, as well as being used as a topical antiseptic or even a food additive.

The biguanide monomer composition of the invention can be incorporated into the functional polymers forming bulk polymer, fiber, fabric, film, aqueous dispersions, solvent-based solutions, etc. Such polymer materials can take the form of the functional polymer providing the mechanical strength in the fiber, fabric, or film bulk polymer or polymeric material, resulting from the use of aqueous solution solvents, etc.

In such a material, the monomer of the invention can be used in amounts of less than 50 mole percent of the polymer, preferably less than 25 mole percent of the polymer, most preferably about 10 mole percent of the polymer material.

As a result, the fiber, fabric, film, bulk polymer, adhesive, coating, sealant formed using the biguanide-containing polymers of the invention, are inherently antimicrobial and require no additional antimicrobial for protection from unwanted growth of organisms. However, it is envisioned that, in certain circumstances, other biocidal materials can be used in conjunction with the polymers of the invention depending on the use locus and the organism found.

A surface that can be coated with an antimicrobial polymeric film of the invention will be essentially self-sanitizing. Coatings of the instant antimicrobial composition can be used on any porous or nonporous, hard or flexible surface which may require an antimicrobial character such as those found in homes, hospitals, schools, in the work place, on marine surfaces, on the human body and the like. The biocidal polymers of the invention can also be used in polymeric compositions that comprise degradable natural polymers.

The instant antimicrobial composition may be applied to a surface in a number of ways. The antimicrobial polymer can be dissolved in a suitable solvent, preferably an organic or aqueous solvent. The antimicrobial solutions can be applied to a surface by a number of methods, including wiping the composition onto a surface with a cloth or a pre-impregnated sponge. The composition may also be poured onto a surface and spread with a mop, squeegee, sponge, or cloth. The polymeric composition may be dispensed from a container equipped with a pump or spray mechanism. The polymeric composition may also be dispensed as an aerosol using a propellant from a suitably pressurized container. The polymeric composition may also be applied by dipping the intended surface of application into a solution of the material. The polymeric composition may also be provided in a sufficient concentration on a cloth or other absorbent carrier and packaging the pre-moistened carrier for disposable use.

Hard surfaces useful for coating with the instant polymeric films include surfaces composed of refractory materials such as glazed and unglazed tile, brick, porcelain, ceramics, metals, glasses, and hard plastic, such as formica, polystyrene, vinyls, acrylics, polyesters, polycarbonates, polyaramides, and the like. The liquid compositions are preferably coated at a thickness sufficient to form a residual film of about 0.01-5 millimeters in final thickness. As an antimicrobial polymeric agent in bulk materials, the material can be used at a concentration of about 0.001 to about 1 wt-%.

MONOMER

The monomeric materials used in preparing the biocidal polymers of the invention can be made by preparing an asymmetric biguanidine compound wherein the active ether amine portion or the active polymerizable group forms the balance of the asymmetric guanide structure. The synthesis of the asymmetrical biguanide material begins with the synthesis of a monoguanido compound of the formula (III):

wherein Z is any substituent upon which a polymerizable group can be linked such as an alkyl or aryl moiety, and can also be a polymerizable group.

The monoguanido compound can be formed by reacting a mono or diamine with a dicyanamide salt, sodium dicyanamide($NaN(CN)_2$) being preferred. Mono or diamines are used because reaction with a dicyanamide compound requires an active hydrogen for reaction to form the monoguanido compound. The preferred mono or diamines for use in this invention are amines that contain polymerizable groups or can easily be derivatized to introduce polymerizable groups into the amine compound.

Examples of such amines are monoethanolamine, diethanolamine, amino phenol, an amine-substituted styrene, a carboxylic acid-substituted alkyl group, a halogen-substituted alkyl group, a diamine compound such as ethylene diamine, phenylene diamine, etc.; an amino acid, an amino acid functionalized as in an amide compound, and others.

The resulting product is a substituted guanido compound. The guanido-substituted alkyl or aryl compound is then reacted further with a monoamine or a diamine compound including mono or dialkyl amines having a $C_1-12$ alkyl group, such as methylamine, ethylamine, diethylamine, dihexylamine, etc., a carboxylic acid containing substituents such as aminobenzoic acid, amino acids, 6-amino-hexanoic acid, 11-amino-undecanoic acid.

The preferred amines for use in the invention is an amine of the formulae (IVa and IVb):

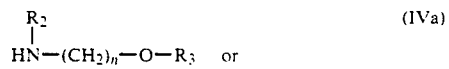

wherein $n=1-12$, x is halogen; wherein $R_2$ is H or a $C_{1-24}$ branched or unbranched alkyl group and $R_3$ is H or a $C_{1-5}$ branched or unbranched alkyl. After the reaction a product is formed according to the general formulae (Va and Vb):

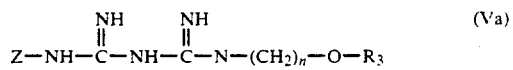

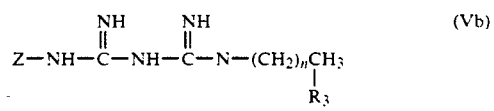

wherein the groups are as defined above.

Generally, amines that can be reacted with the dicyanamide compound to form the biguanido substituted compounds include mono and diamines having functional groups that can be reacted to form polymerizable groups or include mono or diamines having existing polymerizable functional groups. Substituted amines having functional groups that can be used to introduce polymerizable groups into the material include ethylene diamine, diethylene triamine, ethanolamine, diethanolamine, paraminophenol, phenylene diamine, cyclohexanolamine, amino acids such as glycine, prolene, glutanic acid, etc. Amino acid compounds can also be formed in amide functionality.

The active ether amine portion of the asymmetrical biguanide structure can be formed by reacting the substituted biguanido compound at the nitrile (or cyano) functionality with an ether amine compound or a perfluoro alkyl amine compound such as $-NH-(CF_2)_n-CF_3$ wherein $n=1-24$ shown above as Formulae Va and Vb. The preferred ether amine compounds comprise a compound of the formula (VI):

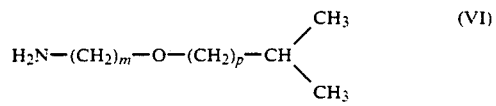

wherein m is an integer of 1 to 4 and p is an integer of 3 to 21. The most preferred ether amine compounds are compounds of the formula (VII):

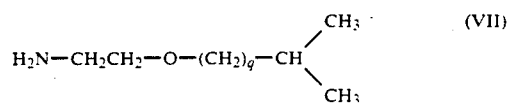

wherein q is an integer of 4 to 16.

In the preferred perfluoro alkylamine compound, $-NH(CF_2)_nCF_3$, n is an integer of about 1 to 20.

The R moiety may also be an amino acid moiety. Preferred amino acid moieties include groups having the structure —CHR'COOH wherein R' is any naturally occurring amino acid side chain. Preferred amino acid moieties include glycine, alanine, serine, threonine, asparagine, glutamine, and histidine wherein R' is the respective side chain of these amino acids.

Returning to the structures of Va and Vb, Z may be any number of species, but is generally phenylene with a polymerizable species A attached thereto (VIII):

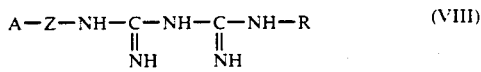

(VIII)

wherein A may comprise any polymerizable moiety like a vinyl moiety such as n-allyl amide or allyl alcohol; an isocyanate moiety; an epoxy moiety such as

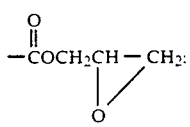

an aziridine moiety such as

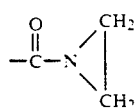

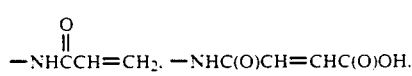

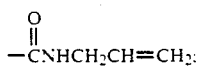

reactive hydrogen carrying moiety, —H, —OH, —NH$_2$, —COOH, or an aliphatic carbon moiety (CH$_2$)$_{1-26}$ terminated with any of these reactive hydrogen containing groups.

The acrylic amide moieties are generally preferred due to their predictable reactivity and ready commercial availability. In synthesizing monomer (VIII) where A is an amide, as defined above, an unsymmetrical biguanidine is generally used as a starting stock where Z is phenyl and A is either a reactive carboxyl group (—COOH) or a reactive nitrile group (—NH) attached to the phenyl, and para to the biguanidine structure.

Any number of reactive monomeric constituents may then be used to synthesize a monomer having a combined acrylic and amide functionality. Several preferred mechanisms have been found.

First, the unsymmetrical biguanidine having a nitrile and carboxyl functionality in the A position may be used to synthesize monomer (IX), (X) and (XI) through the following mechanisms:

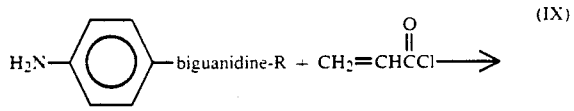

(IX)

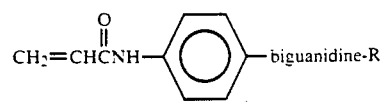

wherein methacryloyl chloride is reacted with an unsymmetrical biguanidine feedstock in the presence of a tertiary base such as triethylamine resulting in monomer (IX);

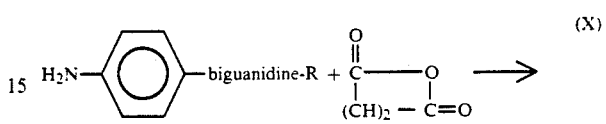

(X)

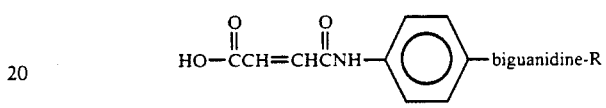

wherein maleic anhydride is reacted with an unsymmetrical biguanidine feedstock resulting in monomer (X);

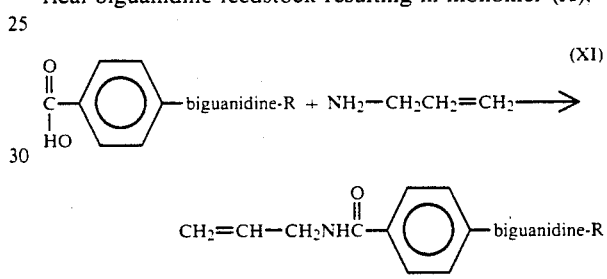

(XI)

wherein n-allyl amine is reacted with an unsymmetrical biguanidine feedstock in the presence of a catalyst such as dicyclohexylcarbodiimide resulting in monomer (XI). Similarly any of the other vinyl moieties referenced having sufficient activity to propagate a polymer chain such as those earlier may be affixed to the monomer in the A position of compound (VIII).

Similar to the synthesis resulting in monomer (XI), the same unsymmetrical biguanidine feedstock, having a reactive carboxyl moiety in the A position may be reacted with an alkoxy silane such as that of formula NH$_2$(CH$_2$)$_3$—Si—(OR$_3$)$_3$ wherein R$_3$ is ethyl or methyl to provide a monomer of the formula (XII):

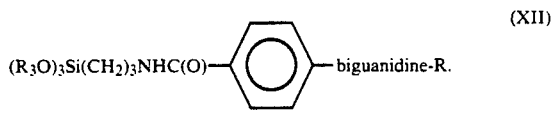

(XII)

Generally, monomers of the present invention of formula XII are most preferably applied into a film system by applying the monomers onto the intended surface under ambient conditions. The monomers then polymerize in situ by hydrolyzing to form polysiloxanes either through weak acids inherently present on the surface or through a minimal amount of acid catalyst.

Monomers of formula (XII) may also be copolymerized with other polymerizable monomers through redox catalysis or other radical polymerizations or photo initiated polymerizations known to those of skill in the art to provide single or multilayer contiguous or laminate structures.

The polymerizable compound of the present invention also includes epoxy and aziridine moieties in the A position of formula (VIII). For example, an epoxy monomer may be synthesized by combining a feedstock of unsymmetrical biguanidine with a glycidyl ether epoxy ($CH_2OCHCH_2OH$). In this instance the 1,3, and 5 nitrogens of the biguanidine chain may be blocked with an agent such as trifluoro acetic anhydride during the synthesis of the monomer. The resulting monomer has the formula (XIII):

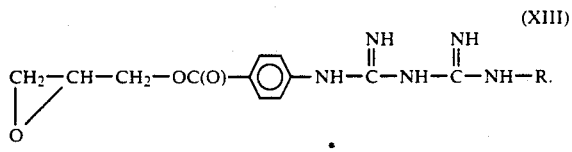

In providing monomer (XIII), appropriate esterification catalysts may also be useful such as, for example para-toluene sulfonic acid or N,N dimethyl amino pyridine.

Aziridine moieties may also be attached in the A position formula (VIII) of the monomer of the present invention. In this instance, the monomer of formula (XIV) is synthesized from simple aziridine and an unsymmetrical biguanidine feedstock in the presence of an organic solvent. The resulting monomer has the following formula (XIV):

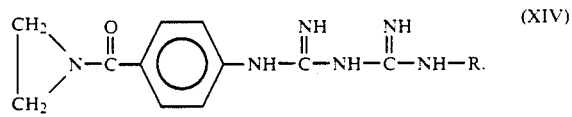

In this instance, similar blocking agents and reaction catalysts may be used to successfully provide the monomer of formula (XIV).

Simple reactive hydrogen containing moieties or aliphatic alkyl moieties which contain pendent reactive hydrogen groups through mechanisms such as that shown above, using an aromatic feedstock having the polymerizable moiety in place prior to the synthesis of the biguanidine. Representative aromatics include benzoates, phenolics, analines and the like.

COMONOMERS

Polymerizable unsymmetrical biguanide compounds of the invention typically contain at least one vinyl polymerizable group permitting the inclusion of the biocidal monomer in a vinyl polymeric material. The vinyl unsaturated monomer of the invention can be copolymerized with a variety of other vinyl unsaturated monomers including alpha olefins, and other olefinic hydrocarbons including ethylene, propylene, butylene, isobutylene, 1-hexene, 3-hexene, etc.; vinyl acetate and other vinyl carboxylic acid ester; acrylic monomers including acrylic acid, methacrylic acid, acrylamide, methacrylamide, methylacrylate, methyl methacrylate, hydroxyalkyl acrylate, hydroxyalkyl methacrylate, butyl acrylate, hexylmethacrylate, cyclohexyl acrylate, etc.; alpha, beta unsaturated dicarboxylic acids and anhydrides such as itaconic acid, aconitic acid, cinnamic acid, crotonic acid, mesaconic acid, maleic acid, maleic anhydride, fumaric acid, and the like; alpha, beta-unsaturated dicarboxylic acid esters of the dicarboxylic acids described above including aromatic esters, cycloalkyl esters, alkyl esters, hydroxyalkyl esters, alkoxyalkyl esters, and others.

As used herein, the term "cycloalkyl ester" includes mono, bi and tricycloalkyl esters and the term "aromatic ester" includes heteroaromatic esters.

Preferred cycloalkyl and aromatic esters are those of acrylic acid, methacrylic acid or maleic acid and anhydride. Useful aromatic esters of these acids include phenyl, benzyl, tolyl, tetra hydrofurfuryl, and phenoxy ethyl esters. Useful cycloalkyl esters include ($C_5$-$C_{12}$) cycloalkyls, e.g., the cyclohexyl, cyclopentyl, isobornyl and adamantyl esters of the acids mentioned above. Preferred (hydroxy)alkyl ester comonomers include (2-hydroxyethyl)methacrylate, (2-hydroxyethyl)ethacrylate, (2-hydroxyethyl)acrylate, (3-hydroxypropyl)methacrylate, (3-hydroxypropyl)acrylate, or (3-hydroxypropyl)ethacrylate.

Examples of useful ($C_5$-$C_{12}$) alkyl esters include hexyl, octyl, ethylhexyl, isodecyl, and lauryl acrylates, methacrylates and itaconates. Examples of (alkoxy)alkyl esters useful as comonomers include (C1-$C_4$)alkoxy-($C_1$-$C_4$)alkyl esters of acrylic, methacrylic or itaconic acids such as (methoxy)ethyl, (ethoxy)ethyl, (methoxy)propyl, (ethoxy)propyl, and the like. Examples of suitable esters include (2-hydroxyethyl) acrylate or methacrylate, (hydroxypropyl) acrylate or methacrylate, (dimethylamino-ethyl)methacrylate, (piperidinoethyl) methacrylate, (morpholinoethyl)methacrylate, methacrylylglycolic acid, the monomethacrylates of ethylene glycol, glycerol, and of other polyhydric alcohols, the monomethacrylates of dialkylene glycols and polyalkylene glycols, etc. Alpha, beta-unsaturated amides may also be copolymerized with the vinyl unsaturated compound of the invention including acrylamide, methacrylamide, diacetone acrylamide, methylol acrylamide, methylol methacrylamide, and the like.

Such polymerizations are typically formed in either solvent polymerization systems or inverse emulsion systems using a suitable solvent such as organic C4 alkanols, lower ketones, such as acetone, methyl ethyl ketone, ethyl acetate tetrahydrofuran (THF), and the like. Preferred solvents are non-toxic and odorless. The monomeric starting materials used to form the biocidal polymers of the invention are typically dissolved or suspended in the solvent to a desired concentration. Preferably the polymerizations of the invention typically are performed at a concentration of about 10-50 wt-% of the monomers in the solvent material although somewhat higher or lower concentrations may be employed in some cases.

Polymerization reactions are typically initiated in the conventional manner, preferably by use of a suitable initiator. Examples of suitable initiators include azobisisobutonitrile, 2,2'-azobis(2-methylpropanenitrile) (AIBN), dibenzoyl peroxide, tertiary butyl peroctoate, cumene hydroperoxide, diisopropyl percarbonate, ammonium persulfate, and the like, per se, or in combination with a reducing agent in the form of an oxidation reduction catalysis system. During the course of the reaction, the reaction mixture may be agitated and heated preferably in an inert (nitrogen or argon) atmosphere, to about 50-100° C., controlling the reaction temperature to avoid destructive exotherms, preferably to about 75-95° C. After completion of the copolymerization reaction, a solution of the polymer can be applied to the target surface without substantial purification or concentration, or can be collected, purified or redissolved in another solvent. Some care should be taken to ensure that no polymerization initiator remains in active form in the reaction mixture.

APPLICATIONS

The polymerizable monomer of the present invention may be used in polymers finding any number of applications. Generally, the concentration of the monomer is sufficient to provide the spectrum of activity desired for any intended use. More specifically, of the polymer composition, the monomer of the present invention is about 1 wt-% to 90 wt-%, preferably 1 wt-% to 50 wt-%, and most preferably 2 wt-% to 30 wt-%. The resulting polymer may be used in emulsion or solution systems providing an effective monomer concentration generally about 0.01 wt-% to 60 wt-% and most preferably 0.1 wt-% to 50 wt-%.

The polymer of the present invention may be used within film formers such as adhesives, in surface cleaners, in topical scrubs, in coating compositions, personal care products, pump or aerosol sprays, sealants and the like, among other compositions. Polymers may be synthesized through any variety of polymerization methods including emulsion polymerization, graft polymerization, solvent polymerization and the like.

In film forming compositions such as adhesives, the polymer of the present invention may be formulated directly into either a solvent based or aqueous system by simple mixing or copolymerization. The polymer of the present invention may be used to thwart the growth of deleterious microbials in adhesives such as for example, hydrogels comprising polysaccharides which are largely susceptible to microorganisms contamination.

Other adhesive compositions such as pressure sensitive adhesives may also comprise the polymer of the present invention as an antimicrobial agent. In this instance, acrylates such as ethyl or hexylmethacrylate are formulated into a latex emulsion. The polymer is then copolymerized or added neat to the composition. Generally, the polymer of the present invention may be used at concentrations which provide adequate antimicrobial activity across the intended spectrum. The film forming agents comprising the polymer of the present invention may be used in systems such as elastic bandages, bandage adhesives, as well as any number of other adhesive compositions or film agents.

The polymer of the present invention may also be used in antimicrobial films such as teat dips. In this instance, the polymer of the present invention would be formulated into an aqueous composition having a high viscosity comprising other agents such as surfactants, carboxylic acids, and the like. Here again, the polymer of the present invention may be used in concentrations intended to provide broad spectrum antimicrobial activity.

The polymer of the present invention may also be used in aqueous or organic solutions which are intended to be applied as surface cleaners to porous and nonporous substrates. In this instance, the surface cleaner may comprise any number of constituents including buffers, surface active agents, defoaming agents, and the polymer of the present invention at a concentration which is effective in providing a broad spectrum of antimicrobial action or antiviral action.

The polymer of the present invention may also be used in topical scrubs which comprise surfactants, simple fatty acids, conditioners, foam builders such as alkanolamides, buffers, etc. In this instance, the polymer of the present invention may have a dual function of preserving the scrub or cleanser and acting as a topical antimicrobial to clean the skin of unwanted contaminants. The concentration of the polymer of the present invention may be adjusted to provide, here again, any range of antimicrobial action appropriate for the intended use, generally using the concentration of a polymer as provided above.

The polymer of the present invention may also be used in coating systems of any non or nonwoven fibers, porous or nonporous substrates, including paper, ceramics, wood, etc., as coatings for filters for ultrafiltration in applications such as pharmaceutical purification, blood transfusions, hemodialysis, as well as plasma phoresis and the like. In this instance, the coating may be applied through dip or spray applications. The coating composition may generally comprise any number of different constituents including silanes, organic solvents such as ethanol, methanol, propanol, and the active monomer of the present invention.

Generally, the coating composition using the polymer of the present invention may be also used on substrates which are silicon reactive such as polyurethanes, polytetrafluoroethylene, polyvinyl chloride, or polyvinylidene fluoride, and the like to provide a system which by its silicon reactivity combines with the silane constituent in the coating composition to effectively lock the active ingredient into the coating polymer across the surface of the substrate. Here again, the concentration of the polymer would vary depending upon the intended application and the spectrum of activity desired of the coating agent.

The polymer of the present invention may also be used in personal care products such as hair and skin conditioners or creams. Such compositions may be desirable for treating various dermal conditions resulting from antimicrobial or viral agents. In this instance, these compositions may comprise any number of constituents including water, long chain fatty acids, conditioning agents, sequestrants and the like.

The polymer of the present invention may also be used in pump or aerosol spray compositions to be applied as a sanitizing or disinfecting coating or solution. In this instance, the polymer of the present invention is a highly appropriate constituent as it generally has a molecular weight highly suitable for pump or aerosol spray application.

In addition to the polymer of the present invention these compositions would generally also comprise water, sequestrants if needed, and depending upon the system of application, any variety of commercially available propellants.

The polymer of the present invention may also be used in any variety of sealants such as caulks, grouts, mortars, and the like. One application among many of the polymer of the present invention is its use in biomedical sealants appropriate for application to medical conditions such as colostomies. For example, the polymer of the present invention may be used in adhesives which are intended to seal a colostomy bag to a patient's port or stoma. In this instance the need for an antimicrobial to maintain the consistency of the adhesive is especially pronounced given the passage of various fluids and materials from the intestines of the patient which may have any variety of antimicrobials therein.

Also, the polymer of the present invention may be used in sealants such as caulks, grouts and mortars found in any variety of applications which may be subjected to antimicrobial attack. For example, sealants used in cement docks at ocean fronts or lake fronts are often subjected to degradation and fouling by micro and macroorganisms. Sealants comprising the compound of the present invention would not only deter the formation and incrustation by macroorganisms but also maintain the consistency of the sealant.

Exemplary compositions are those again comprising any number of acrylics including methacrylate, methylmethacrylate, hydoralkylacrylate, hydroxyalkylmethacrylate, butylacrylate, hexylacrylate, cyclohexylacrylate, cyclohexylacrylate, (2-hydroxyethyl)ethacrylate, (2-hydroxyethyl)ethacrylate, (2hydroxyethyl)acrylate, (3-hydroxypropyl)ethacrylate, (3-hydroxylpropyl)acrylate, (3-hydroxypropyl)ethacrylate, (dimethylamino-ethyl)ethacrylate, (pipiridinoethyl)methacrylate, (morpholinoethyl)methacrylate and the like. These acrylics are generally preformed into a latex emulsion system with the active compound of the present invention blended in to the emulsion after it is formed.

Other applications of polymers of the present invention include the production of self-sterilizing medical plastics. Compositions such as these can be produced through the copolymerization of polymers of the present invention with polyacrylics such as polyvinyl chloride or any other polyacrylic that will copolymerize with the active polymer at the appropriate temperature. Self-preserving medical films may also be synthesized by grafting polymers of the present invention onto polyvinyl systems such as polyethylene or polypropylene. Another application of the active polymers of the present invention includes grafting these polymers onto polyester and polyamide systems for the manufacture of biocompatible implantable medical devices.

As can be seen, the polymer of the present invention may be used to obtain enhanced antimicrobial activity in any variety of compositions which are used in various applications including health care, food preparation, sanitation and cleaning, the construction industries, and the personal care products industry. However, these compositions and applications should not be looked at as limiting, rather as exemplary of the versatility of the polymer of the present invention.

The following Examples illustrate the preparation of the monomer and polymers of the present invention including its use in certain final applications including personal care products, medical products, and antimicrobials generally. These working examples should be viewed simply and purely as illustrative and not as limiting of the present invention.

EXAMPLE I

Synthesis of 4-cyanoguanidino phenol was initiated by charging into a 200 milliliter round bottom flask equipped with a reflux condenser and heater with 100 milliliters of water containing 5.3 grams of sodium dicyanamide NaN(CN)$_2$ (0.06 mole). After the dicyanamide compound was dissolved 8.7 grams of paraminophenol chloride (0.6 mole). The mixture was refluxed at ambient pressure for 30 minutes. At the end of the reaction a purple fluffy mass was observed in the reflux container which was washed with 2 liters of water, 1 liter of acetone and then dried under vacuum. The IR spectrum in (Nujol-Mull) of the sample is consistent with the structure:

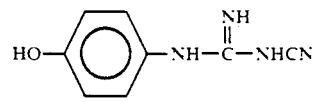

Specifically the infrared spectrum showed two sharp peaks located at about 3430 cm$^{-1}$ and 3370 cm$^{-1}$ represent NH and OH groups. Also C=N and C≡N were observed in the spectrum. Both proton and carbon 13 nuclear magnetic resonance spectra obtained on the compound were entirely in agreement with the structure shown above. The table below gives carbon number assignments and C-13 chemical shifts with respect to deuterated DMSO at 39.79 ppm.

TABLE 1

| C-13 Chemical Shift Table | |
|---|---|
| Carbon Number | δ $^{13}$C, ppm |
| 1 | 160.5 |
| 2 | 155.1 |
| 3 | 129.2 |
| 4 | 125.2 |
| 5 | 118.2 |
| 6 | 115.8 |

EXAMPLE II

Synthesis of N-1 hydroxyphenol, N-5 undecanoic acid biguanidine was initiated by adding into a 50 milliliter round bottom flask equipped with a reflux condenser and a nitrogen inert atmosphere, 25 milliliters of dimethylformamide, 5 grams of para-cyanoguanidino phenol (Example I), and a stoichiometric amount of 11-amino undecanoic acid hydrochloride salt. The mixture was maintained at 155° C. for 3.5 hours while the reaction was monitored using thin layer chromatography. One major compound appeared during the reaction. The contents of the reaction flask were diluted with 50 ml isopropanol containing 0.2 equivalents of potassium hydroxide. The unreacted 11-amino undecanoic acid precipitate was filtered out, leaving the monomer having a formula shown through infrared and NMR analysis to be:

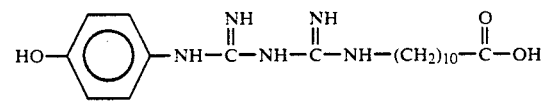

Infrared analysis showed consumption of the nitrile peak at 220 cm$^{-1}$, strong imine absorbance at 1660 cm$^{-1}$, moderate carboxylic acid absorbtion at 1440 cm$^{-1}$ and 2600–3000 cm$^{-1}$. aliphatic absorbance at 1520 cm$^{-1}$. The C$_{13}$NMR analysis supported these results and the preceding structure.

EXAMPLE III

To make the monomer of Example II polymerizable, one equivalent of Example II monomer is added to a reactor charged with 50 ml isopropanol also containing one equivalent of n-allyl amine and one equivalent of triethyl amine. One equivalent of dicyclohexyl carbodiimide is then added to the reactor followed by stirring until a voluminous mass of dicylcohexyl urea (DCU) is formed. The DCU is then filtered out of the system and the pH is adjusted to a value of 2-4. The mixture is then extracted with 1 to 2 volumes of hexane and the solvents and unreacted precursors are then removed by vacuum distillation. The polymerizable monomer is:

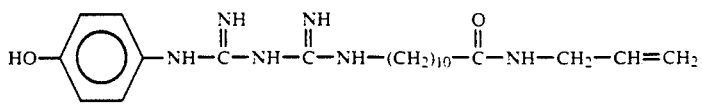

EXAMPLE IV

Preparation of water soluble copolymer of product of Example III is initiated by charging into a 500 milliliter round bottom, three neck flask equipped with a mechanical stirrer, 15 grams of isopropanol, 180 milligrams of azobisisobutyronitrile, and 30 grams of monomer mixture comprising 10% of the product of Example III and 90% of 2-vinyl pyrolidone.

The polymerization is conducted by initially reacting 5% of the monomer mixture, the reaction temperature is raised to 75° C. and the remaining monomer mixture is introduced drop-wise over a 2-hour period with constant agitation. The temperature is held constant and agitation continued for 24 hours. When polymerization is complete the solvent is evaporated and the residue is extracted with hexane to remove unreacted precursors. The polymer may then be dissolved in any chosen aqueous or organic solvent.

EXAMPLE V

An N-allyl amide of an acidic peptide biguanide was synthesized by dissolving 15 g, (0.031 mole), of β-alanyl benzoyl biguanide in 35 ml methanol, after which 6.3 g, (0.030 moles), of dicyclohexylcarbodiimide and 1.76 g (0.032 mole) of allylamine were added. The reaction mixture was stirred for 1 hour at room temperature. The insoluble dicylcohexyl urea was filtered off and the supernatant was extracted with 3 volumes of hexane.

CNMR showed evidence of loss of acid carbon at 173 ppm and the appearance of an alpha and beta unsaturated amide at about 166 ppm. This data coupled with the thin layer chromatograph and infrared spectrum, showing evidence of a substituted olefin at 990 cm$^{-1}$ supports the conclusion that the desired alkyl amide was obtained:

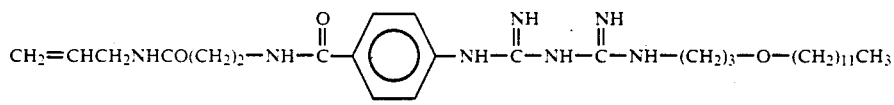

EXAMPLE VI

Synthesis of a polyvinyl pyrrolidone-biguanide copolymer was initiated by charging 15 g isopropyl alcohol into a three-neck reaction vessel with drop funnel, reflux condensor, and mechanical agitator, and 0.18 g of polymerization initiator, azoisobutyronitrile (AIBN) was slowly dissolved in the solvent as the temperature was brought to 60° C. A 5%–95% (W/W) mix of the N-allyl amide-β alanyl benzoyl biguanidine and vinyl pyrrolidone (1.5 g:28.5 g) was prepared, of which 2 g was initially charged into the reactor. The temperature was slowly brought to 65° C. and the remaining monomer mix was introduced over an hour period. Temperature was held constant over the remaining four hour reaction time while the agitation rate was adjusted to compensate for increase in viscosity as polymer formation proceeded. The resulting polymer exhibited good water solubility, easily dissolving up to 5% (W/W).

Antimicrobial analysis of the polymer of Example VI was then undertaken to determine the minimum bacteriocidal concentration of polymer to *E. Coli;* (ATCC 11229). The reduction in bacteria is expressed in logs in Table 2:

TABLE 2

| Minimum Cidal Concentration EXAMPLE VI | | |
|---|---|---|
| CONCENTRATION | 0 Hr. | 24 Hrs. |
| 10 ppm | 1.05 | 0.01 |
| 100 ppm | 0.96 | 3.22 |
| 200 ppm | 1.90 | >4.20 |

The polymer showed significant bacteriocidal capabilities after 24 hours at 100 ppm and 200 ppm concentrations.

EXAMPLE VII

Synthesis of a biguanide-hydroxypropylacrylate copolymer was initiated by charging a three-necked round bottom flask with 15 grams of isopropanol and 0.18 grams of reaction initiator, azoisobutyronitile (AIBN) was slowly dissolved in the solvent as the temperature was brought to 68° C. A 5%–95% (W/W) mix of biguanide monomer and hydroxypropylacrylate (HPA) (1.5 gm of Example V monomer and 28.5 gm of HPA) was then prepared with 5% of this mix added to the reaction vessel immediately and the remainder of this mix added over a 90 minute period. The temperature in the mixing vessel was then held at 70° C. for 6 hours. The polymer was then finalized by precipitation to remove unreacted reaction precursors, the precipitate was characterized by bioassay and GPC.

Antimicrobial analysis showed minimal efficacy at polymer concentrations of 10 ppm, 100 ppm, and 200 ppm over a 24 hour period. Antimicrobial efficacy will increase if the polymer is emulsified with a hydrophilic constituent which facilitates wetting.

EXAMPLE VIII

A latex emulsion containing the monomer of Example V was prepared by adding 34.55 wt-% of water and 0.9 wt-% of sodium bicarbonate buffer to a jacketed vented mixing vessel equipped with feed inlets. The charge was heated to 65° C. under nitrogen purge. At 65° C. 0.16 wt-% each of potassium persulfate and sodium metabisulfite as a catalyst was added to the vessel. A monomer feed of water (16.74 wt-%), surfactant (octylphenoxy polyethoxy ethanol 4.00 wt-%), methylmethacrylate (18.92 wt-%), butylacrylate 19.78 wt-%), methacrylic acid (0.88 wt-%), and the Example V monomer (4.40 wt-%), was then dripped into the vessel over a 3 hour time period. An additional 0.16 wt-% of potassium persulfate and sodium metabisulfite was added concurrent with the monomer addition. The reaction was held one hour at 65° C. after all ingredients were added. The composition was then cooled and discharged into appropriate containers.

EXAMPLE IX

Synthesis of a monoether benzoate biguanidine was initiated by first preparing isododecyl oxypropyl cyanoguanidine. Then 21 g, (0.144 mole) of S,S-dimethyl cyanoimide dithiocarbonate was dissolved in 50 mil isopropanol and 15 ml aqueous ammonia. The reaction mixture was stirred overnight at room temperature. A white crystalline product was collected and recrystalized from isopropanol. The composition had a melting point of 177° C. (175-176° C.) and infrared analysis disclosed nitrile at 2200 cm$^{-1}$, thioether at 1430 cm$^{-1}$.

The N-cyano, S-methyl isothiourea prepared above was then warmed in 15 ml ethanol to dissolve 6.0 g (0.0513). One equivalent of the ether amine isododecyl oxypropylamine, 12.97 g (0.051 mole) was added into the section mixture and stirred overnight at room temperature. The product, a pale yellow oil, was diluted into one volume of ethyl acetate and washed 3 times with 2 volumes water, and aqueous sodium bicarbonate. Infrared analysis disclosed evidence of nitrile at 2200 cm$^{-1}$, imine at 1640 cm$^{-1}$, amidine at 1580 cm$^{-1}$, and aliphatic ether at 1110 cm$^{-1}$.

C$_{13}$NMR analysis disclosed the imine carbon at 161.5 ppm, the nitrile carbon at 118.5 ppm, ether carbons 67.8 and 68.5 ppm. Aliphatic carbons were observable at 20-40 ppm. Additionally, there was no evidence of the presence of a thioether methyl carbon. These data support the conclusion that the desired alkyl ether cyanoguanidine was obtained.

Preparation of the monoether benzoate biguanide was then continued by dissolving 10 g (0.031 moles) of the alky monoether cyanoguanidine in 20 ml THF and adding 5.1 g (0.031 mole) of ethyl amino benzoate and 5 mil con. HCl. Water (10 ml) was then added to solubilize the reactants and the mixture was brought to reflux. After two hours, the nitrile peak at 2200 cm$^{-1}$ was essentially consumed. The product was worked up by extraction into ethyl acetate from dilute aqueous HCl (ph 2.0). If saponification of the ethyl biguanidine ester is desired the monomer may be additionally treated in a 2 N solution of KOH and the free acid is then extracted into any number of water immiscible organic solvents.

Infrared analysis disclosed ester carboxyl at 1720 cm$^{-1}$, strong imine absorption at 1640 cm$^{-1}$ and aliphatic ether at 1110 cm$^{-1}$.

The C$_{13}$NMR analysis disclosed the imine carbons at 160.4 ppm and 165.6 ppm respectively; aromatic carbons at 113.3 ppm, 131.8, 123.8, 143.8 ppm ester carboxyl at 166.4 ppm, ether carbons at 59.6 ppm and aliphatic methylene carbons ranging from 15 ppm to 40 ppm. The aforementioned IR and NMR analysis are consistent with the following structure.

EXAMPLE X

Preparation of chitosan conjugate of a benzoate biguanidine was initiated by obtaining a sample of chitosan (Protan Corp., Redman, Washington; highly polydispersed having a molecular weight ranging from 100,000 to 2,000,000 and containing 7% (by weight) tritratable amine). Based on the information 6.0 g of chitosan should contain 0.026 mole available primary amine for modification with the biguanidine. Assuming a modification level of 25% of the available amino groups on the polymer, 0.0066 mole reagent would be required, or 2.7 g benzoate biguanidine.

To start, 6.0 g chitosan was dissolved in 2% (w/v) acetic acid, 300 ml. at room temperature. The pH was adjusted to 5.0 by addition of sodium acetate. In a separate vessel 4.0 g (50% molar excess over calculated) of the benzoate biguanidine of Example IX was dissolved in 25 ml cellosolve and 2 drops triethylamine was added. Then 1.9 g of 1-ethyl-3 dimethylaminopropylcarbodimide was added in 10 ml water-cellosolve. The activation mixture was incubated for 30 minutes during which the active ester formed. The activated benzoate biguanide was added to the chitosan solution and stirred overnight at room temperature. The chitosan adduct was precipitated two times with acetone and dialyzed against 2000 volumes of 2% acetic acid. This material was then freeze dried. The freeze dried modified chitosan was a waxy friable solid whereas the nature polysaccharide is a fluffy fragile solid material. Upon dissolution in 2% acetic acid the conjugate yields an opalescent solution indicative of a microemulison probably due to the Tyndal effect. By contrast, native chitosan when dissolved in acetic acid yields a solution with high optical clarity. Based on these observations the polysaccharide was most likely acylated by the benzoate biguanidine. The polymer was then subjected to controlled antimicrobial testing which showed that the ocmposition had biocidal efficacy.

EXAMPLE XI

A reactive silane biguanidine was synthesized by first adding 15.5 g, 0.033 mole of the ethyl benzoate biguanide of Example IX into 7.22 g, 0.033 mole, γ-aminopropyltriethyoxysilane and heated in water bath at 150° F. while drawing a slight vacuum of 20 mm mercury, to facilitate removal of evolved ethanol.

The reaction was pushed to completion by addition of a four to five fold under excess of amine silane (21 g). The reaction was monitored by TLC and IR. When the starting biguanide was consumed as judged by TLC, the remaining amine was stripped out at 90° C. at 0.5 mm mercury.

Infrared analysis showed very little residual ester initially observable at 1710 cm$^{-1}$. Additionally a very large absorption at 1600 cm$^{-1}$ indicative of amide can be seen.

C-13 NMR analysis shows evidence of an amide carbonyl at 165.7 ppm with all other resonances for the biguanidine being present. These data support the con-

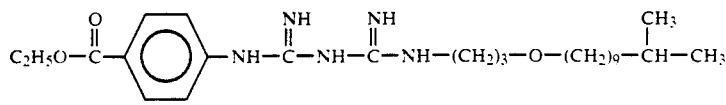

clusion that the desired reactive silane amide was synthesized.

Antibacterial assay was conducted by preparing respective 0.5% w/v solutions of the ethyl benzoate biguanide (Example IX) and the aforementioned reactive silyl benzamide biguanide in methanol. Sufficient aqueous concentrated HCl was added to bring the pH to 4.5. Glass filter fiber discs (47 mm) were dipped in these solutions for laminates at room temperature. Unadsorbed material was washed off in a large volume of methanol. The discs were air dried and autoclaved. The sterile discs were immersed in suspensions of *E. coli* at $10^{10}$ CFU per ml., then placed on nutrient agar and inoculated 18 hours at 37° C. The discs were then washed with sterile saline and dilution aliquots were plated on nutrient agar for enumeration. The results showed that the silane treated discs reduced the bacterial population by five orders of magnitude against the control.

The foregoing specification, Examples and data provide a basis for understanding the invention. The invention can be made in a variety of embodiments without departing from the spirit and scope of the invention. Accordingly the invention resides in the claims hereinafter appended.

I claim as my invention:

1. An antimicrobial polymerizable compound comprising:

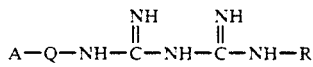

wherein A is a polymerizable group; Q is phenylene; and R is $-(CF_2)_6CF_3$ wherein $y=1-20$, $-(CH_2)_x-O-C_xH_{2x+a}$ wherein $x=1-25$, $-(CH_2CH_2O)_n(CH_2CHCH_3O)_m(CH_2CH_2O)_pT$ wherein $T=-H$ or any branched or unbranched $C_{1-20}$ alkyl and n, m, and $p=0-99$ and $m+n+p\geq 1$, $-CHR'COOH$ wherein R' is H or any naturally occurring amino acid side chain, $-(CH_2)_xCOOH$, $-(CH_2)_x-(CH_2CH_2O)_n-(CH_2CHCH_3O)_m(CH_2CH_2O)_p-CO-NH-CH_2-CH=CH_2$, $-(CH_2)_x-CO-NH-CH_2-CH=CH_2$, or $-(CH_2)_x-O-CO-CH=CH_2)$.

2. The compound of claim 1, wherein A comprises an active polymerizable group selected from $-H$; $-OH$; $-NH_2$; $-COOH$; $(CH_2)_x-R''$ wherein R'' is $-H$, $-OH$, $-NH_2$, $-COOH$; $-NH-CO-CH=CH_2$; $-NH-CO-CH=CH-CO-OH$; $-CO-NH-CH_2-CH=CH_2$;

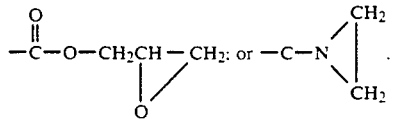

3. The compound of claim 1 wherein A comprises an amino alkoxy silane.

4. The compound of claim 3 wherein the alkoxy silane is selected from the group consisting of gama amino propyl trimethoxysilane, gama amino propyl triethyoxysilane, or gama amino propyl t-butyloxy dimethoxysilane.

5. The compound of claim 2 wherein A is $-NH(CH_2)_xSi(OR_1)_3$ wherein $R_1$ is methyl or ethyl.

6. The compound of claim 1 wherein A comprises a polymerizable vinyl moiety.

7. The compound of claim 6 wherein the polymerizable vinyl moiety is selected from the group consisting of n-allyl amino group, or allyl ether group.

8. The compound of claim 2 wherein R is $-(CH_2)_x-O-C_xH_{2x+1}$ wherein $x=1-25$, or $-(CH_2CH_2O)_n(CH_2CHCH_3O)_m(CH_2CH_2O)_pT$ wherein $T=-H$ or any branched or unbranched $C_{1-20}$ alkyl and n, m, and $p=0-99$ and $n+m+p\geq 1$; and A is $-NH-CO-CH=CH_2$ or $-NH-CO-CH=CH-CO-OH$.

9. A polymer having antimicrobial character comprising a major portion of a first monomer and an antimicrobial effective amount of a second monomer, said second monomer comprising:

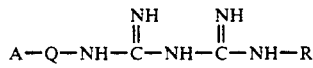

wherein A is an active polymerizable group; Q is phenylene; and R is $-(CF_2)_yCF_3$ wherein $y=1-20$, $-(CH_2)_x-O-C_xH_{2x+1}$ wherein $x=1-25$, $-(CH_2CH_2O)_n(CH_2CHCH_3O)_m(CH_2CH_2O)_pT$ wherein $T=-H$ or any branched or unbranched $C_{1-20}$ alkyl, n, m, and $p=0-99$, and $n+m+p\geq 1$; $-CHR'COOH$ wherein $R_1$ is H or any naturally occurring amino acid side chain, $-(CH_2)_xCOOH$, $-(CH_2)_x-(CH_2CH_2O)_n-(CH_2CHCH_3O)_m(CH_2CH_2O)_p-CO-NH-CH_2-CH=CH_2$, $-(CH_2)_x-CO-NH-(CH_2)_x-CH=CH_2$, or $-(CH_2)_x-O-CO-CH=CH_2$.

10. The polymer of claim 9 wherein A comprises an active polymerizable group selected from $-H$; $-OH$; $-NH_2$; $-COOH$; $(CH_2)_x-R''$ wherein R'' is $-H$, $-OH$, $-NH_2$, $-COOH$; $-NH-CO-CH=CH_2$; $-NH-CO-CH=CH-CO-OH$; $-CO-NH-CH_2-CH=CH_2$; or $$-C(O)-O-CH_2-\underset{\underset{OH}{|}}{CH}-CH_2-O-CH_2-CH=CH_2.$$

11. The polymer of claim 9 wherein A comprises an amino alkoxy silane.

12. The polymer of claim 11 wherein the alkoxy silane is selected from the group consisting of gama amino propyl trimethoxysilane, gama amino propyl triethyoxysilane, or gama amino propyl t-butyloxy dimethoxysilane.

13. The polymer of claim 11 wherein A is $-NH(CH_2)_xSi(OR_1)_3$ wherein $R_1$ is methyl or ethyl.

14. The polymer of claim 9 wherein A comprises a polymerizable vinyl moiety.

15. The polymer of claim 14 wherein the polymerizable vinyl moiety is selected from the group consisting of n-allyl amine or allyl alcohol.

16. The polymer of claim 9 wherein R is $-(CH_2)_x-OC_xH_{2x+1}$ wherein $x=1-25$, or $-(CH_2CH_2O)_n(CH_2CHCH_3O)_m(CH_2CH_2O)_pT$ wherein $T=-H$ or any branched or unbranched $C_{1-20}$ alkyl and n, m, and $p=0-99$ and $n+m+p\geq 1$; and A is $-NH-CO-CH=CH_2$ or $-NH-CO-CH=CH-CO-OH$.

17. The polymer of claim 9 wherein said second monomer is present in a concentration ranging from 2 wt-% to 15 wt-%.

18. The polymer of claim 9 wherein the first monomer comprises a vinyl compound selected from the group consisting of alpha-olefin compounds, acrylic monomers, vinyl aromatic monomers, and alpha-beta unsaturated mono- and di-carboxylic acids and esters thereof.

19. An emulsion latex comprising a major portion of aqueous carrier and the polymer of claim 9.

20. A sealant comprising a sealing composition and the polymer of claim 9.

21. A surface antimicrobial cleaner comprising a carrier and the polymer of claim 9.

22. A topical antimicrobial scrub comprising a surfactant and the polymer of claim 9.

23. A coating comprising a film forming agent and the polymer of claim 9.

24. An adhesive comprising a binder and the polymer of claim 9.

25. A personal care product comprising a conditioner and the polymer of claim 9.

26. A medical article comprising a plastic and the polymer of claim 9.

27. An aqueous polymer latex composition having enhanced antimicrobial efficacy comprising a major portion of water and dispersed therein a polymer comprising a first monomer and an effective antimicrobial amount of a second monomer, said second monomer comprising:

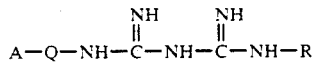

wherein A is an active polymerizable group; Q is phenylene; and R is $-(CF_2)_yCH_3$ wherein $y=1-20$, $-(CH_2)_x-O-C_xH_{2x+1}$ wherein $x=1-25$, $-(CH_2CH_2O)_n(CH_2CHCH_3O)_m(CH_2CH_2O)_pT$ wherein $T=-H$ or any branched or unbranched $C_{1-20}$ alkyl, n, m, and $p=0-99$, $n+m+p \geq 1$, $-CHR'COOH$ wherein R' is H or any naturally occurring amino acid side chain, $-(CH_2)_xCOOH$, $-(CH_2)_x-(CH_2CH_2O)_n-(CH_2CHCH_3O)_m(CH_2CH_2O)_p-CO-NH-CH_2-CH=CH_2$, $-(CH_2)_x-CO-NH-(CH_2)_x-CH=CH_2$, or $-(CH_2)_x-O-CO-CH=CH_2$.

28. The latex of claim 19 wherein A comprises an active polymerizable group selected from $-H$; $-OH$; $-NH_2$; $-COOH$; $-(CH_2)_x-R''$ wherein R'' is $-H$, $-OH$, $-NH_2$, $-COOH$; $-NH-CO-CH=CH_2$; $-NH-CO-CH=CH-CO-OH$; $-CO-NH-CH_2-CH=CH_2$; or

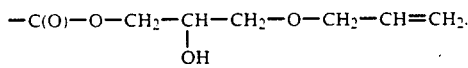

29. The latex of claim 27 wherein A comprises an amino alkoxy silane.

30. The latex of claim 29 wherein the alkoxy silane is selected from the group consisting of gama amino propyl trimethoxysilane, gama amino propyl triethyoxysilane, or gama amino propyl t-butyloxy dimethoxysilane.

31. The latex of claim 29 wherein A is $-NH(CH_2)_xSi(OR_1)_3$ wherein R is methyl or ethyl.

32. The latex of claim 27 wherein A comprises a polymerizable vinyl moiety.

33. The latex of claim 27 wherein the polymerizable vinyl moiety is selected from the group consisting of n-allyl amine, or allyl alcohol.

34. The latex of claim 27 wherein R is $-(CH_2CH_2O)_n(CH_2CHCH_3O)_m(CH_2CH_2O)_pT$ wherein $T=-H$ or any branched or unbranched $C_{1-20}$ alkyl and n, m, and $p=0-99$ and $n+m+p \geq 1$; and A is $-NH-CO-CH=CH_2$ or $-NH-CO-CH=CH-CO-OH$.

35. The latex of claim 27 wherein said second monomer is present in a concentration ranging from 2 wt-% to 15 wt-%.

36. The latex of claim 27 wherein the first monomer comprises a vinyl compound selected from the group consisting of alpha-olefin compounds, acrylic monomers, vinyl aromatic monomers, and alpha-beta unsaturated mono- and di-carboxylic acids and esters thereof.

37. A sealant comprising a sealing composition and the latex of claim 27.

38. A surface antimicrobial cleaner comprising a carrier and the latex of claim 27.

39. A topical scrub comprising a surfactant and the latex of claim 27.

40. A coating comprising a film forming composition and the latex of claim 27.

41. A personal care product comprising a conditioner and the latex of claim 27.

42. A medical article comprising a plastic and the latex of claim 27.

43. A solution polymer composition having enhanced antimicrobial efficacy comprising a major portion of solvent and solubilized therein a polymer comprising a first monomer and an effective antimicrobial amount of a second monomer, said second monomer comprising:

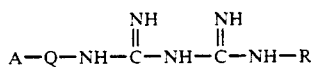

wherein A is an active polymerizable group; Q is phenylene; and R is $-(CF_2)_yCF$; wherein $y=1-20$, $-(CH_2)_x-O-C_xH_{2x+a}$ wherein $x=1-25$, $-(CH_2CH_2O)_n(CH_2CHCH_3O)_m(CH_2CH_2O)_pT$ wherein $T=-H$ or any branched or unbranched $C_{1-20}$ alkyl, and n, m, and $p=0-99$, $n+m+p \geq 1$, $-CHR'COOH$ wherein R' is H or any naturally occurring amino acid side chain, $-(CH_2)_xCOOH$, $-(CH_2)_x-(CH_2CH_2O)_n-(CH_2CHCH_3O)_m(CH_2CH_2O)_p-CO-NH-CH_2-CH=CH_2$, $-(CH_2)_x-CO-NH-CH_2-CH=CH_2$, or $-(CH_2)_x-O-CO-CH=CH_2$.

44. The composition of claim 43 wherein A comprises an active polymerizable group selected from $-H$; $-OH$; $-NH_2$; $-COOH$; $(CH_2)_xR''$ wherein R'' is $-H$, $-OH$, $-NH_2$, $-COOH$; $-NH-CO-CH=CH_2$; $-NH-CO-CH=CH-CO-OH$; $-CO-NH-CH_2-CH=CH_2$; or

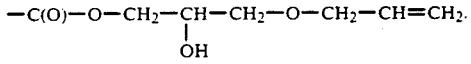

45. The composition of claim 43 wherein A comprises an amino alkoxy silane.

46. The composition of claim 45 wherein the alkoxy silane is selected from the group consisting of gama amino propyl trimethoxysilane, gama amino propyl triethyoxysilane, or gama amino propyl t-butyloxy dimethoxysilane.

47. The composition of claim 45 wherein A is $-NH(CH_2)_xSi(OR_1)_3$ wherein R is methyl or ethyl.

48. The composition of claim 43 wherein A comprises a polymerizable vinyl moiety.

49. The composition of claim 48 wherein the polymerizable vinyl moiety is selected from the group consisting of n-allyl amine, or allyl alcohol.

50. The composition of claim 43 wherein R is $-(CH_2)_x-O-C_xH_{2x+a}$ wherein $x=1-25$, or $-(CH_2CH_2O)_n(CH_2CHCH_3O)_m(CH_2CH_2O)_pT$ wherein $T=-H$ or any branched or unbranched $C_{1-20}$ alkyl and n, m, and $p=0-99$ and $n+m+p \geq 1$; and A is $-NH-CO-CH=CH_2$ or $-NH-CO-CH=CH-CO-OH$.

51. The composition of claim 43 wherein said second monomer is present in a concentration ranging from 2 wt-% to 15 wt-%.

52. The composition of claim 43 wherein the first monomer comprises a vinyl compound selected from the group consisting of alpha-olefin compounds, acrylic monomers, vinyl aromatic monomers, and alpha-beta unsaturated mono- and di-carboxylic acids and esters thereof.

53. A sealant comprising the composition of claim 43.

54. A surface antimicrobial cleaner comprising the composition of claim 43.

55. A topical antimicrobial scrub comprising the composition of claim 43.

56. A coating comprising the composition of claim 43.

57. A personal care product comprising the composition of claim 43.

58. A medical article comprising the composition of claim 43.

* * * * *

UNITED STATES PATENT AND TRADEMARK OFFICE
CERTIFICATE OF CORRECTION

PATENT NO. : 5,142,010

DATED : August 25, 1992

INVENTOR(S) : Alan D. Olstein

It is certified that error appears in the above-identified patent and that said Letters Patent is hereby corrected as shown below:

In Column 3, line 12, after "$CH_2$,", insert

-- $-NHC(O)CH=CHC(O)-OH$, or $-C(O)NHCH_2CH=CH_2$ --.

In Column 7, line 66, "-" should read -- + --.

In Column 8, line 27, "-" should read -- + --.

In Column 17, line 51, after "$1720 cm^{-1}$,", insert -- $1280 cm^{-1}$ --.

In Column 19, line 35, "$-(CF_2)_6 CF_3$" should read -- $-(CF_2)_y CF_3$ --.

In Column 19, line 36, "$-C_x H_{2x}-_a$" should read -- $-C_x H_{2x+1}$ --.

In Column 19, line 54, "-C-N" should read -- -CO-N --.

In Column 20, line 9, after "CH", delete "-".

In Column 20, line 26, "R," should read -- R' --.

In Column 21, line 31, "$CH_3$" should read -- $CF_3$ --.

In Column 22, line 35, "CF:" should read -- $CF_3$ --.

In Column 22, line 36, "-a" should read -- +1 --.

In Column 22, line 43, after "$CH_3$", delete "( )" and insert -- 0) --.

UNITED STATES PATENT AND TRADEMARK OFFICE
CERTIFICATE OF CORRECTION

PATENT NO. :     5,142,010

DATED      :     August 25, 1992

INVENTOR(S) :    Alan D. Olstein

It is certified that error appears in the above-identified patent and that said Letters Patent is hereby corrected as shown below:

In Column 22, line 49, "NH:," should read -- $NH_2$, --.

In Column 22, line 66, "R" should read -- $R_1$ --.

In Column 23, line 5, "-a" should read -- +1 --.

Signed and Sealed this

Ninth Day of November, 1993

Attest:

BRUCE LEHMAN

*Attesting Officer*     Commissioner of Patents and Trademarks